United States Patent [19]
Gonzalez et al.

[11] Patent Number: 5,382,706
[45] Date of Patent: Jan. 17, 1995

[54] PRODUCTION OF ALKYL TERT ALKYL ETHERS AND CATION EXCHANGE RESIN FOR SAME

[75] Inventors: Jose C. Gonzalez, Austin, Tex.; Leonardo Escalante, San Antonio De Los Altos - Edo Miranda; Raicelina Ramos, Charallave Edo Miranda, both of Venezuela

[73] Assignee: Intevep, S.A., Caracas, Venezuela

[21] Appl. No.: 128,383

[22] Filed: Sep. 29, 1993

[51] Int. Cl.$^6$ .................................. C07C 41/06
[52] U.S. Cl. .......................... 568/697; 502/159
[58] Field of Search .............................. 568/697

[56] References Cited

U.S. PATENT DOCUMENTS

| | | |
|---|---|---|
| 4,330,679 | 5/1982 | Köhler et al. |
| 4,695,556 | 9/1987 | Oeckl et al. |
| 5,008,466 | 4/1991 | Schleppinghoff et al. |
| 5,084,070 | 1/1992 | Köhler et al. |

*Primary Examiner*—Howard T. Mars
*Attorney, Agent, or Firm*—Bachman & LaPointe

[57] ABSTRACT

A process for preparing alkyl tert alkyl ethers includes the steps of providing a liquid olefinic hydrocarbon feedstock having a sulfur content, providing an ion exchange resin containing an amount of palladium selected based upon the sulfur content of the liquid olefinic hydrocarbon feedstock, mixing the liquid olefinic hydrocarbon feedstock with alcohol and hydrogen so as to obtain a reaction feedstock and treating the reaction feedstock with the ion exchange resin under etherification conditions so as to obtain an alkyl tert alkyl ether.

19 Claims, 2 Drawing Sheets

PRODUCTION OF ALKYL TERT ALKYL ETHERS AND CATION EXCHANGE RESIN FOR SAME

BACKGROUND OF THE INVENTION

The invention relates to the preparation of alkyl tert alkyl ethers and, particularly, to a process for preparing alkyl tert alkyl ethers from liquid olefinic hydrocarbon feedstock containing sulfur and to an ion exchange resin for use in the process.

Alkyl tert alkyl ethers such as methyl t-butyl ether (MTBE) ethyl t-amyl ether (TAME) ethyl t-butyl ether (ETBE) and the like are used as fuel extenders and octane value improving agents to produce unleaded gasoline having acceptable octane values without varying the compounding ratio of the gasoline.

Alkyl tert alkyl ether additives serve as substitutes for lead anti-knock compounds. Because lead anti-knock compounds yield undesirable emissions from the exhaust gas of a combustion engine, substitution of additives according to the invention provides reduced environmental pollution.

Alkyl tert alkyl ethers are typically produced by reacting a primary alcohol with an olefin having a double bond on a tertiary carbon atom. For example, methanol can be reacted with isobutylene to form methyl t-butyl ether (MTBE), and with isopentene to form methyl t-amyl ether (TAME). Ethanol, as another example, can be reacted with isobutylene to form ethel t-butyl ether (ETBE).

The reaction to form alkyl tert alkyl ethers is catalyzed by Lewis acids such as sulfuric acid, and organic acids such as alkyl and aryl sulfonic acids and ion exchange resins. Ion exchange resins in acid form are particularly useful, and macroporous cation exchange resins doped with or otherwise containing hydrogenation metals of groups VI, VII and VIII provide good results.

However, typical feedstocks for the reaction such as light hydrocarbon streams from FCC operations have been found to rapidly deactivate the resin during etherification, thereby making the process inefficient and costly. Examples of known processes for preparing alkyl tert alkyl ethers are disclosed in U.S. Pat. No. 4,330,679 to Köhler et al., U.S. Pat. No. 4,695,556 to Oeckl et al., U.S. Pat. No. 5,008,466 to Schleppinghoff et al. and U.S. Pat. No. 5,084,070 to Köhler et al.

However, none of the foregoing patents provides a process which addresses the problem of rapid ion exchange resin deactivation.

It is therefore the principal object of the invention to provide a process for preparing alkyl tert alkyl ethers wherein the ion exchange resin is not rapidly deactivated.

It is another object of the invention to provide a process for etherification of a light hydrocarbon stream wherein a high quality raffinate byproduct is provided for downstream use in alkylation processes.

It is still another object of the invention to provide an ion exchange resin for use in preparation of alkyl tert alkyl ethers wherein the resin is resistant to deactivation.

Other objects and advantages will appear hereinbelow.

SUMMARY OF THE INVENTION

According to the invention, it has been found that sulfur, particularly certain types of sulfur, cause a rapid deactivation of ion exchange resin during etherification processes. It has also been found that deactivation of the catalyst due to sulfur contained in the feedstock can be avoided by doping or otherwise providing the resin with an amount of palladium which is determined based upon the amount and type of sulfur compound contained in the feedstock.

According to the invention, the process for producing alkyl tert alkyl ethers comprises the steps of providing a liquid olefinic hydrocarbon feedstock having a sulfur content, providing an ion exchange resin containing an amount of palladium selected based upon said sulfur content of said liquid olefinic hydrocarbon feedstock, mixing said liquid olefinic hydrocarbon feedstock with alcohol and hydrogen so as to obtain a reaction feedstock and treating said reaction feedstock with said ion exchange resin under etherification conditions so as to obtain an alkyl tert alkyl ether.

The proper amount of palladium depends upon the amount and type of sulfur contained in the feedstock. According to the invention, the sulfer of the feedstock is quantified in terms of an equivalent amount of mercaptan, which is particularly damaging to ion exchange resins for etherification processes. The mercaptan sulfur equivalent (MSE) of the feedstock is determined as follows: $MSE = M + 5 \cdot (H_2S) + 5 \cdot (COS) + 0.25 \cdot (D) + 0.1 \cdot (OCS)$, wherein MSE is the mercaptan sulfur equivalent of sulfur in said liquid olefinic hydrocarbon feedstock, in sulfur wt. ppm; M is the sulfur content of said liquid olefinic hydrocarbon feedstock in the form of mercaptan, in sulfur wt. ppm; $H_2S$ is the sulfur content of said liquid olefinic hydrocarbon feedstock in the form of hydrogen sulfide, in sulfur wt. ppm; COS is the sulfur content of said liquid olefinic hydrocarbon feedstock in the form of carbonyl sulfide, in sulfur wt. ppm; D is the sulfur content of said liquid olefinic hydrocarbon feedstock in the form of disulfide, in sulfur wt. ppm; and OCS is the sulfur content of said liquid olefinic hydrocarbon feedstock in the form of other sulfur compounds, in sulfur wt. ppm.

The ion exchange resin is preferably doped or otherwise provided with palladium in an amount of between about $(Pd)_{min}$ and $(Pd)_{max}$. $(Pd)_{min}$ is a minimum amount of palladium measured as grams of palladium per liter of dry resin, and can be determined as follows: $(Pd)_{min} = 0.065 \cdot (MSE) + 0.1$, wherein MSE is said mercaptan sulfur equivalent $(Pd)_{max}$ is a maximum amount of palladium measured as grams of palladium per liter of dry resin, and can be determined as follows: $(Pd)_{max} = 0.08 \cdot (MSE) + 2$, wherein MSE is said mercaptan sulfur equivalent.

In further accordance with the invention, an ion exchange resin for etherification of sulfur containing liquid hydrocarbon feedstock comprises a macroporous polystyrene resin cross linked with divinylbenzene and containing an amount of palladium sufficient to prevent sulfur deactivation of the resin by sulfur contained in the liquid olefinic hydrocarbon feedstock.

BRIEF DESCRIPTION OF THE DRAWINGS

A detailed description of the preferred embodiments of the invention follows with reference to the attached drawings, wherein.

DETAILED DESCRIPTION

Figure 1:
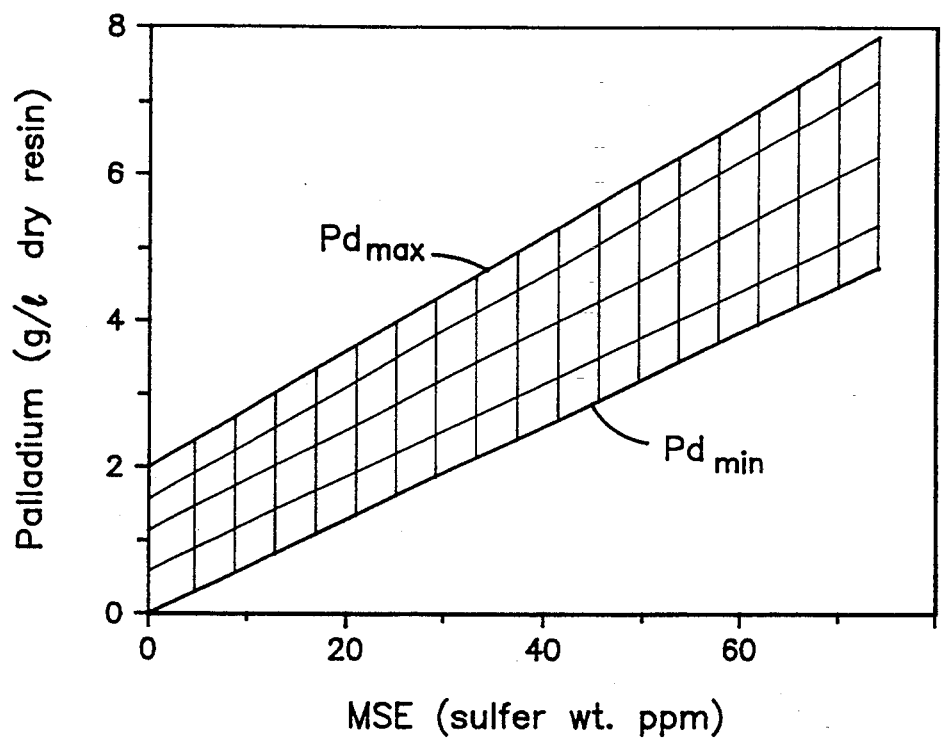
FIG. 1 illustrates an optimum doping of the resin per mercaptan equivalent of sulfur in the feedstock.

The invention relates to a process for producing alkyl tert alkyl ethers from light hydrocarbon streams and to an ion exchange resin for use in producing alkyl tert alkyl ether.

Alkyl tert alkyl ethers are useful as substitutes for lead anti-knock additives in gasoline. Alkyl tert alkyl ethers are typically prepared by reacting a primary alcohol with an olefin having a double bond on a tertiary carbon atom. The etherification process is accelerated by known catalysts including ion exchange resins which may be doped with hydrogenation metals selected from Groups VI, VII or VIII of the periodic table of elements.

According to the invention, it has been found that the deactivation of conventional ion exchange resins is frequently caused by sulfur contained in the hydrocarbon feedstock. It has also been found that deactivation can be effectively inhibited by doping the ion exchange resin with effective amounts of palladium and that the amount of palladium to be used depends not only on the amount of sulfur in the feedstock but also on the form of the sulfur in the feedstock.

According to the invention, alkyl tert alkyl ethers such as MTBE, TAME, ETBE and the like are produced by mixing a liquid olefinic hydrocarbon feedstock with appropriate amounts of alcohol and hydrogen to obtain a reaction feedstock and treating the reaction feedstock with an ion exchange resin containing an amount of palladium which is determined or optimized based upon the sulfur content of the feedstock. In particular, an amount of palladium is selected for use based upon a mercaptan equivalent of sulfur (MSE) in the feedstock which is determined according to the invention as will be set forth below.

Preferred feedstocks for the process include light hydrocarbon streams such as $C_4$–$C_{10}$ FCC streams, $C_4$–$C_{10}$ coking process streams, $C_4$–$C_{10}$ steam cracking process streams, light naphtha FCC streams containing $C_3$–$C_7$, preferably $C_4$ and $C_5$, and the like. The feedstock may preferably have a composition as follows:

| | |
|---|---|
| isobutene | 0.1–25 wt % |
| isoamylene | 0.1–30 wt % |
| diolefin | 0.2–2.5 wt % |
| other $C_4$ and $C_5$ | 50–90 wt % |
| sulfur | up to about 300 ppm |

The sulfur content of the feedstock typically includes mercaptan in an amount up to about 80 ppm by weight of sulfur, $H_2S$ in an amount up to about 5 ppm, carbonyl sulfide (COS) in an amount up to about 5 ppm, disulfide in an amount up to about 50 ppm, and the balance as other sulfur containing compounds.

The alcohol to be mixed with the liquid olefinic hydrocarbon feedstock should be selected based upon the desired alkyl tert alkyl ether, and may preferably be a primary alcohol selected from the group consisting of methanol, ethanol, propanol, isopropanol, butanol, isobutanol and the like.

The alcohol used determines, to some extent, the resulting alkyl tert alkyl ether. For example, reaction of methanol with isobutene or isoamylene, respectively, provides methyl t-butyl ether (MTBE) or methyl t-amyl ether (TAME) respectively. Reaction of ethanol with isobutene or isoamylene, respectively, yields ethyl t-butyl ether (ETBE) or ethyl t-amyl ether (ETAE) respectively. Further, various combinations of alcohol and feedstock may be used to provide a mixture of several different alkyl tert alkyl ethers.

Alcohol is preferably mixed with the liquid olefinic hydrocarbon feedstock so as to provide a molar ratio of alcohol to tertiary olefin contained in the feedstock of between about 0.5 to about 3.0.

Hydrogen is preferably mixed with the liquid olefinic hydrocarbon feedstock in amount sufficient to hydrogenate diolefins contained in the feedstock, preferably in amounts sufficient to provide a molar ratio of hydrogen to diolefin in the feedstock of between about 0.5 to about 4.0.

The liquid olefinic hydrocarbon feedstock, primary alcohol and hydrogen are mixed as above so as to provide a reaction feedstock suitable for treatment with the ion exchange resin to provide alkyl tert alkyl ether.

The ion exchange resin is preferably a macroporous polystyrene resin cross linked with divinylbenzene and containing palladium in an amount based upon the sulfur contained in the feedstock. According to the invention, the resin is more severely affected by mercaptan sulfur than other types of sulfur. In accordance with the process of the invention, therefore, palladium is utilized based upon a mercaptan sulfur equivalent (MSE) of the sulfur in the feedstock which is determined as follows:

$$MSE = M + 5.(H_2S) + 5.(COS) + 0.25.(D) + 0.1.(OCS),$$

wherein

MSE is the mercaptan sulfur equivalent of the sulfur in the liquid olefinic hydrocarbon feedstock, in sulfur wt. ppm; M is the sulfur content of said liquid olefinic hydrocarbon feedstock in the form of mercaptan, in sulfur wt. ppm; $H_2S$ is the sulfur content of said liquid olefinic hydrocarbon feedstock in the form of hydrogen sulfide, in sulfur wt. ppm; COS is the sulfur content of said liquid olefinic hydrocarbon feedstock in the form of carbonyl sulfide, in sulfur wt. ppm; D is the sulfur content of said liquid olefinic hydrocarbon feedstock in the form of disulfide, in sulfur wt. ppm; and OCS is the sulfur content of said liquid olefinic hydrocarbon feedstock in the form of other sulfur compounds, in sulfur wt. ppm.

The resin is doped with a minimum amount of palladium $(Pd)_{min}$ which is determined as follows:

$$(Pd)_{min} = 0.065.(MSE) + 0.1,$$

wherein $(Pd)_{min}$ is said minimum amount of palladium measured as grams of palladium per liter of dry resin; and MSE is said mercaptan sulfur equivalent.

Palladium is added up to a maximum preferable amount, $(Pd)_{max}$, determined as follows:

$$(Pd)_{max} = 0.08.(MSE) + 2,$$

wherein $(Pd)_{max}$ is said maximum amount of palladium measured as grams of palladium per liter of dry resin; and MSE is said mercaptan sulfur equivalent. Palladium may preferably be provided in an amount between about 0.1 to about 10.0 grams of Pd per liter of dry resin for typical feedstocks. The resin preferably contains divinylbenzene in an amount ranging between about 5 to about 65 wt % by weight of the resin.

In accordance with the invention, alkyl tert alkyl ether may be produced as follows. A suitable stream of liquid olefinic hydrocarbon is provided. A sample of the stream can be taken and analyzed to determine its composition including sulfur content and the form of the sulfur in the stream. From this information, the mercaptan sulfur equivalent (MSE) can be obtained. A proper ion exchange resin may then be prepared containing an appropriate amount of palladium based upon the sulfur content or MSE of the feedstock.

The resin is preferably doped with a suitable amount of palladium, then activated by washing with water at an elevated temperature, and then dehydrated with methanol preferably until a water content of less than 1 wt % is achieved. Palladium reduction may be carried out, for example, at a temperature of about 90° C., a pressure of about 15 bar gauge, and a methanol flow rate of about 1100 ml/hr for 24 hours.

The resin so prepared may typically have physical properties as follows:

| Acid Sites: | 1-7 equivalents/liter |
|---|---|
| Porosity: | 0.1–0.5 cc/g |
| Pore Diameter: | 100–500 Å |
| Surface Area: | 15–100 m²/g |
| Paticle Size: | 0.1–3 mm |

The feedstock selected as above is mixed with appropriate amounts of alcohol and hydrogen so as to provide a reaction feedstock having the desired molar ratios as set forth above. The reaction feedstock is then treated with the resin at effective etherification conditions to provide the desired alkyl tert alkyl ether. Typical process conditions may include a pressure of between about 10 to about 25 bars gauge, a temperature of between about 40° C. to about 90° C., and a liquid hourly space velocity of reaction feedstock to resin of between about 0.5 to about 5.0 v/v/hour.

In accordance with the invention, the palladium prevents sulfur in the feedstock from causing rapid deactivation of the catalyst resin. Without palladium, the sulfur deactivates the metal active phase of a conventional catalyst or resin. The metal active phase is responsible for hydrogenation of diolefins and, if the metal active phase is deactivated, the diolefins tend to polymerize instead. The polymerization of diolefins leads to the formation of gum which then fouls the resin, reducing the capacity of the resin to formation of double bond isomerization, thereby reducing ether yield and also reducing the quality of the raffinate by-product of the process.

Resins formulated and utilized in accordance with the present invention avoid the foregoing problem. The advantages of the invention are further highlighted by the following examples.

EXAMPLE 1

This example demonstrates the relatively stable operation of a resin on a feedstock which has a relatively low sulfur content and which is essentially free of mercaptan.

The test was run in a pilot plant with a fixed bed reactor. The reactor was externally heated with oil circulated through a jacket. Reactive mixture was fed to the reactor in an upflow mode using a membrane pump. Sampling analyzers were located downstream and upstream of the reactor to analyze feedstock and products.

A C5 olefinic cut obtained from a FCCU (Fluid Catalytic Cracking Unit) was mixed with methanol (99.8 wt % purity) to form the reactive mixture. A small amount of hydrogen required for the hydrogenation and isomerization reactions was mixed with the reactive mixture before feeding it to the reactor. The reaction feedstock properties were:

| Methanol content | 13.9 wt % |
|---|---|
| 3 methyl 1 butene content | 0.69 wt % |
| 2 methyl 2 butene content | 11.94 wt % |
| 2 methyl 1 butene content | 5.41 wt % |
| TAME reactive Isoamylenes (2M1B + (2M2B) | 17.35 wt % |
| Isoprene content | 0.29 wt % |
| Total diolefin content | 1.01 wt % |
| Pentene 1 content | 2.75 wt % |
| Other hydrocarbon content | approx. 64 wt % |
| Mercaptan sulfur content | less than 1 wt ppm |
| Total sulfur content | 10 wt ppm |
| (MSE) | 1 wt ppm sulfur |

Two similar ion exchange resins loaded with different amounts of palladium were used.

Resin A was doped with 3 gr of Pd per liter of resin.
Resin B was doped with 1 gr of Pd per liter of resin.

Catalyst activation was achieved by washing the resins at 25 degrees celsius using 10 volume of water per volume of resin. Then the resins were dehydrated with methanol until the water content was less than 1 wt percent. Palladium reduction was carried out under the following condition: temperature of 90 degrees celsius, pressure of 15 bar gauge, methanol flow 1100 ml/hr during 24 hr.

The test was run in the pilot plant with a reactor loaded with 267 ml of Pd doped cation exchange resin. Each resin was tested in the plant as described above and under the following reactions conditions, and the results obtained are shown in Table 1.

Reaction conditions
Pressure 15 bar gauge.
LHSV: 3 v/v/h (relative to doped resin).
Recycle ratio: 1 vol of reactor product/vol of fresh feedstock.
Reactor inlet temperature 60 degrees celsius.

TABLE 1

| RESIN TESTED | A | B |
|---|---|---|
| $H_2$/diolefin ratio (mole/mole) | 2.0 | 2.0 |
| Diolefin conversion (wt %) | 100 | 100 |
| Isoprene conversion (wt %) | 100 | 100 |
| 3 methyl 1 butene conversion (wt %) | 71.4 | 72.5 |
| Pentene 1 conversion (wt %) | 74.9 | 68.3 |
| TAME yield (mole TAME/mole react. Isoamylne feed) | 0.65 | 0.63 |

Table 1 shows that resin B (1 g of Pd/lt resin) performs as good as resin A (3 g of Pd/lt of resin) when the feedstock has a low content of sulfur and is essentially free of mercaptan. This is observed by the complete diolefin hydrogenation and the very high levels of conversion of pentene 1 and 3 methyl 1 butene (isomerization). As seen, resin B is adequate for this application while resin A is overdoped.

EXAMPLE 2

This test was run to demonstrate that a feedstock with different sulfur content needs an appropriate formulation of metal doping the ion exchange resin to achieve good yield and to avoid catalyst deactivation.

The test was run in a pilot plant as in Example 1 but with two fixed bed reactors. The reactors were loaded with 267 ml of Pd doped ion exchange resin.

A C5 olefinic cut obtained from a FCCU (Fluid Catalytic Cracking Unit) was mixed with methanol (99.8 wt % purity) to form the reactive mixture. The feedstock had a significant content of sulfur, being 50% of the mercaptan type. A small amount of hydrogen required for the hydrogenation and isomerization reactions was mixed with the reactive mixture before feeding it to the reactor. The reaction feedstock properties were:

| | |
|---|---|
| Methanol content | 12.4 wt % |
| 3 methyl 1 butene content | 1.07 wt % |
| 2 methyl 2 butene content | 1.24 wt % |
| 2 methyl 1 butene content | 6.6 wt % |
| TAME reactive Isoamylenes | 18.84 wt % |
| Isoprene content | 0.44 wt % |
| Total diolefin content | 1.31 wt % |
| Pentene 1 content | 3.41 wt % |
| Other hydrocarbon content | approx. 62.5 wt % |
| Mercaptan sulfur content | 25 wt ppm (mainly ethyl and isopropyl mercaptan) |
| Disulfide sulfur: | 13 wt ppm |
| Total sulfur content (MSE) | 50 wt ppm 29 wt ppm sulfur |

The same two ion exchange resins loaded with different amounts of palladium as used in example 1 were used.

Resin A was doped with 3 gr of Pd per liter of resin.
Resin B was doped with 1 gr of Pd per liter of resin.
Catalyst activation was achieved by the same procedure as in Example 1.

In the pilot plant described above and under the following reaction conditions, each resin was tested and the results obtained are shown in Table 2.

Pressure: 15 bar gauge
LHSV: 4 v/v/h (relative to doped resin)
Recycle ratio: 1 vol of reactor product/vol of fresh feedstock
Reactor inlet average temperature 68 degrees C
$H_2$/diolefin ratio 2.0 mol/mol

TABLE 2

| RESIN TESTED | A | B |
|---|---|---|
| Diolefin conversion (wt %) | 100 | 81.5 |
| Isoprene conversion (wt %) | 100 | 85.2 |
| 3 methyl 1 butene conversion (wt %) | 57.0 | 0.0 |
| Pentene 1 conversion (wt %) | 62.6 | 14.3 |
| TAME yield (mole TAME/mole react. Isoamylne feed) | 0.629 | 0.589 |

Table 2 shows that resin B (1 g of Pd/lt resin) was unable to fully hydrogenate diolefin and gave a very low isomerization conversion of pentene 1 and 3 methyl 1 butene. It is clear from data shown in Table 2 that resin A (3 g of Pd/lt of resin) is more appropriate for feedstock with a significant sulfur content. In this case resin B is underdoped.

EXAMPLE 3

This example was run to demonstrate the life of a cation exchange resin properly formulated with the amount of doped metal depending on the amount of sulfur in the feedstock used.

The test was run in a pilot plant as in Example 1 with a fixed bed reactor. Product samples were taken periodically during each test to follow the catalyst activity. The reactor was loaded with 267 ml of a Pd doped ion exchange resin.

A C5 olefinic cut obtained from a FCCU (Fluid Catalytic Cracking Unit) which was spiked with 25 wt ppm of mercaptan sulfur (n-butyl mercaptan) was mixed with methanol (99.8 wt % purity) to form the reactive mixture. A small amount of hydrogen required for the hydrogenation and isomerization reactions was mixed with the reactive mixture before feeding it to the reactor. The reaction feedstock properties were:

| | |
|---|---|
| Methanol content | 13.71 wt % |
| 3 methyl 1 butene content | 0.92 wt % |
| 2 methyl 2 butene content | 9.76 wt % |
| 2 methyl 1 butene content | 5.23 wt % |
| TAME reactive Isoamylenes (2M1B + 2M2B) | 14.99 wt % |
| Isoprene content | 0.42 wt % |
| Total diolefin content | 1.35 wt % |
| Pentene 1 content | 2.74 wt % |
| Other hydrocarbon content | approx. 65.8 wt % |
| Mercaptan sulfur content | 25 wt ppm (n-C4 mercaptan) |
| Disulfide sulfur: | 13 wt ppm |
| Total sulfur content (MSE) | about 35 wt ppm 26 wt ppm sulfur |

The same two cation exchange resins loaded with different amounts of palladium as used in Example 1 were used.

Resin A was doped with 3 gr of Pd per liter of resin.
Resin B was doped with 1 gr of Pd per liter of resin.
Catalyst activation was achieved by the same procedure as in Example 1.

Figure 2:
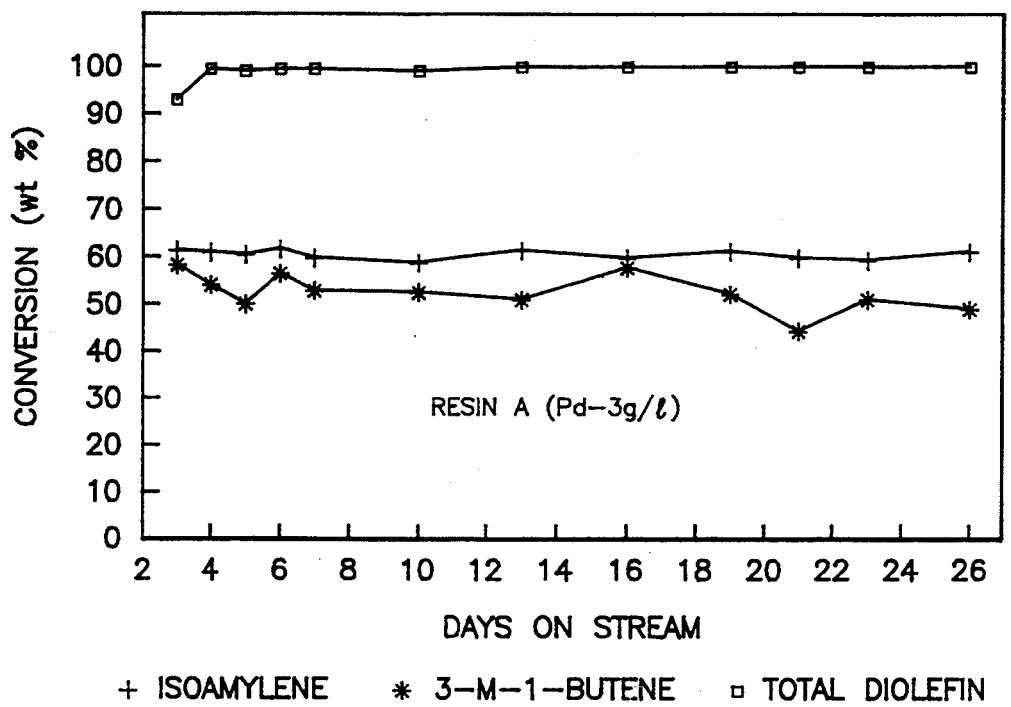
FIG. 2 illustrates the conversion provided by a resin having an amount of palladium determined according to the invention.
Figure 3:
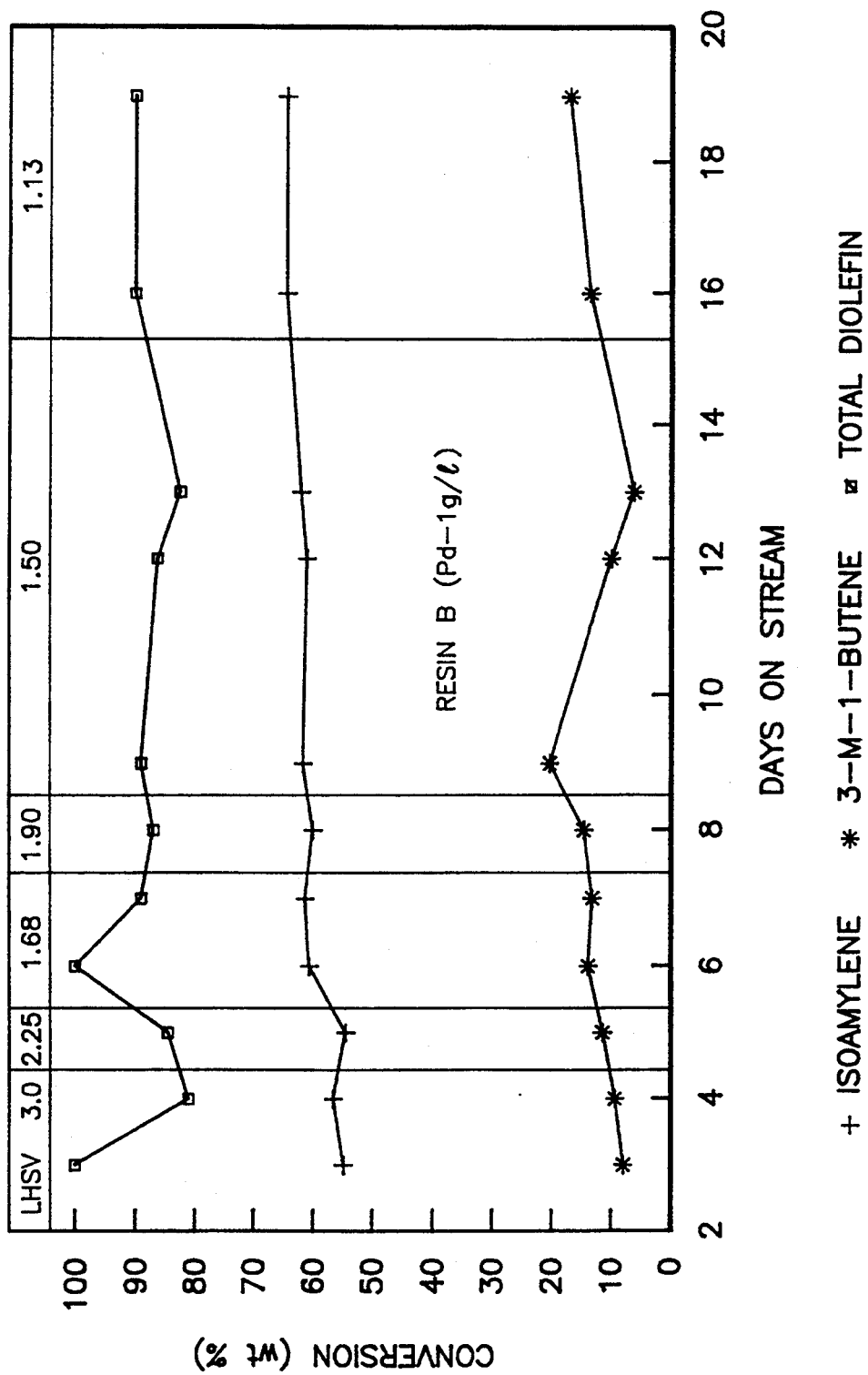
FIG. 3 illustrates the conversion provided by a resin having an insufficient amount of palladium.

In the pilot plant described above and under the following reaction conditions, each resin was tested and the results obtained are shown in FIGS. 2 and 3.

Pressure 15 bar gauge.
LHSV Res in A: 3 v/v/h (relative to metal doped resin).
LHSV Resin B: 1.5 v/v/h (relative to metal doped resin).
Recycle ratio: 1 vol of reactor product/vol of fresh feedstock.
Reactor inlet average temperature 67 degrees C.
$H_2$/diolefin ratio 2.0 mol/mol.

It can be seen from FIGS. 2 and 3 that catalyst A (3 gr of Pd/lt of resin) shows a very good stability for the conversion of diolefin by hydrogenation and for the isomerization of 3 methyl 1 butene for about one month of operation while catalyst B (1 gr of Pd/lt of resin) required continuous reduction of the space velocity to values equivalent to ⅓ of the value used for catalyst A in order to make it suitable for processing the feedstock with higher sulfur content compounds.

EXAMPLE 4

This example was run to demonstrate results obtained with a resin doped with 3 gr of Pd per liter of resin for treatment of feedstock having different amounts of mercaptan sulfur. The effect was tested over the conversion of diolefins and double bond isomerization.

A pilot plant was used identical to that of Example 3.

A feedstock was used which was similar to Example 1 but spiked with different content of n-butyl mercaptan as follows:

25 wt ppm of mercaptan sulfur (35 ppm of total sulfur)

40 wt ppm of mercaptan sulfur (50 ppm of total sulfur)

50 wt ppm of mercaptan sulfur (60 ppm of total sulfur)

The same resin as in Example 1 was used.

OPERATION CONDITIONS AND RESULTS

The reaction conditions were:
Pressure 15 bar gauge.
LHSV Resin A: 3 v/v/h (relative to metal doped resin).
Recycle ratio: 1 vol of reactor product/vol of fresh feedstock.
Reactor inlet average temperature 67 degrees C.
$H_2$/diolefin ratio 2.0 mol/mol.

The results obtained testing resin A with the feedstock are shown in Table 3.

TABLE 3

| MERCAPTAN SULFUR EQUIVALENT | 26 | 41 | 51 |
|---|---|---|---|
| Diolefin conversion (wt %) | 100 | 100 | 83.7 |
| Isoprene conversion (wt %) | 100 | 100 | 87.4 |
| 3 methyl 1 butene conversion (wt %) | 54.2 | 35.7 | 3.1 |
| Pentene 1 conversion (wt %) | 61.4 | 51.9 | 15.4 |
| TAME yield (mole TAME/mole react. Isoamylne feed) | 0.690 | 0.663 | 0.562 |

The results show that if double bond isomerization is not critical, catalyst A (3 gr of Pd/liter of resin) which had a good performance processing 26 ppm of MSE sulfur can be used with 41 ppm of MSE sulfur in the feed. While still providing complete diolefin hydrogenation. However if the feed has 50 ppm of MSE sulfur, catalyst A does not perform satisfactorily.

EXAMPLE 5

This example was run to demonstrate behavior of an ion exchange resin doped with 3 g Pd per liter of resin for treating a feedstock with very high sulfur content different than that of the mercaptan type.

A pilot plant was used which was identical to Example 3.

The feedstock was similar to Example 1 but spiked with thiophene and dimethyl sulfide as follows:
100 wt ppm of thiophene sulfur.
100 wt ppm of dimethyl sulfide sulfur.
Total sulfur content 210 wt ppm.
(MSE)=21 wt ppm.

The catalyst was resin A as in Example 1.
The resin was tested under the following reaction conditions:
Pressure 15 bar gauge.
LHSV Resin A: 3 v/v/h (related to doped resin).
Recycle ratio: 1 vol of reactor product/vol of fresh feedstock.
Reactor inlet average temperature 72 degrees C.
$H_2$/diolefin ratio 2.0 mol/mol.

The results obtained testing resin A with each feedstock are shown in Table 4.

TABLE 4

| Diolefin conversion (wt %) | 100 |
|---|---|

TABLE 4-continued

| Isoprene conversion (wt %) | 100 |
|---|---|
| 3 methyl butene 1 conversion (wt %) | 46.6 |
| Pentene 1 conversion (wt %) | 53.5 |
| TAME yield (mole TAME/mole react. Isoamylnes feed) | 0.56 |

Table 4 shows that even though the feed was spiked with a very high total amount of sulfur (200 wt ppm), the hydrogenation and isomerization activity of resin A was reasonably high. In Example 4 it was shown that resin A does not perform well when the feed is spiked with 50 ppm of mercaptan sulfur. This demonstrates that mercaptan sulfur is a more severe poison to the catalyst than thiophene and sulfide compounds.

EXAMPLE 6

This test was run to show the production of MTBE and TAME with a feedstock with a significant amount of thiophenic sulfur and other sulfur species different than mercaptan type.

A pilot plant was used which was similar to Example 3. A second membrane pump was added to the plant in order to feed methanol (99.8% purity) as a separate stream to the reactor.

A C4-C5 olefinic cut from FCCU with the following properties:

| Isobutylene content | 6.48 wt % |
|---|---|
| 3 methyl 1 butene content | 0.90 wt % |
| 2 methyl 2 butene content | 6.21 wt % |
| 2 methyl 1 butene content | 4.19 wt % |
| TAME reactive Isoamylnes (2M1B + 2M3B) | 10.40 wt % |
| Isoprene content | 0.20 wt % |
| Total diolefin content | 0.76 % |
| Butene 1 content | 5.63 wt % |
| Pentene 1 content | 2.11 wt % |
| Other hydrocarbons | 63.12 wt % |
| Mercaptan sulfur content | less than 1 wt ppm |
| Disulfide sulfur content | 1.5 wt ppm |
| Total sulfur content | 87 wt ppm |
| (MSE) | 9 wt ppm sulfur |

Resin B was doped with 1 gr of Pd per liter of resin as in Example 1.

The resin was tested under the following reaction conditions:
Pressure 18 bar gauge.
LHSV Resin B: 3 v/v/h (related to doped resin).
Recycle ratio: 1 vol of reactor product/vol of fresh feedstock.
Reactor inlet average temperature 64 degrees C.
$H_2$/diolefin ratio: 2.0 mol/mol.
Methanol/isoamylene and isobutylene ratio: 13 mol/mol.

The results obtained testing resin B with the feedstock are shown in Table 5.

TABLE 5

| Diolefin conversion (wt %) | 100 |
|---|---|
| Isoprene conversion (wt %) | 100 |
| 3 methyl 1 butene conversion (wt %) | 18 |
| Butene 1 isomerization conv. (wt %) | 39 |
| Pentene 1 conversion (wt %) | 33 |
| TAME yield (mole TAME/mole react. Isoamylnes feed) | 0.560 |
| MTBE yield (mole MTBE/mole react. Isobutylene feed) | 0.958 |

Table 5 shows that even though the amount of sulfur of the feedstock is relatively high (almost 90 wt ppm), this sulfur species is mainly thiophenic and does not have a severe poisoning effect on the resin as does mercaptan sulfur species. For this reason the low Palladium resin B was able to hydrogenate all the diolefin, even though the isomerization of butene 1, pentene 1 and 3M1B was relatively low.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A process for preparing alkyl tert alkyl ethers, comprising the steps of:
    providing a liquid olefinic hydrocarbon feedstock having a sulfur content;
    providing an ion exchange resin containing an amount of palladium selected based upon said sulfur content of said liquid olefinic hydrocarbon feedstock;
    mixing said liquid olefinic hydrocarbon feedstock with alcohol and hydrogen so as to obtain a reaction feedstock; and
    treating said reaction feedstock with said ion exchange resin under etherification conditions so as to obtain an alkyl tert alkyl ether.

2. A process according to claim 1, wherein said mercaptan sulfur equivalent (MSE) is determined according to the following:

$$MSE = M + 5 \cdot (H_2S) + 5 \cdot (COS) + 0.25 \cdot (D) + 0.1 \cdot (OCS),$$

wherein
    MSE is the mercaptan sulfur equivalent of the sulfur in the liquid olefinic hydrocarbon feedstock, in sulfur wt. ppm;
    M is the sulfur content of said liquid olefinic hydrocarbon feedstock in the form of mercaptan, in sulfur wt. ppm;
    $H_2S$ is the sulfur content of said liquid olefinic hydrocarbon feedstock in the form of hydrogen sulfide, in sulfur wt. ppm;
    COS is the sulfur content of said liquid olefinic hydrocarbon feedstock in the form of carbonyl sulfide, in sulfur wt. ppm;
    D is the sulfur content of said liquid olefinic hydrocarbon feedstock in the form of disulfide, in sulfur wt. ppm; and
    OCS is the sulfur content of said liquid olefinic hydrocarbon feedstock in the form of other sulfur compounds, in sulfur wt. ppm.

3. A process according to claim 2, further including doping said resin with at least about a minimum amount of palladium $(Pd)_{min}$ determined as follows:

$$(Pd)_{min} = 0.065 \cdot (MSE) + 0.1,$$

wherein
    $(Pd)_{min}$ is said minimum amount of palladium measured as grams of palladium per liter of dry resin; and
    MSE is said mercaptan sulfur equivalent.

4. A process according to claim 3, further including doping said resin with no greater than about a maximum amount of palladium $(Pd)_{max}$ determined as follows:

$$(Pd)_{max} = 0.08 \cdot (MSE) + 2,$$

wherein
    $(Pd)_{max}$ is said maximum amount of palladium measured as grams of palladium per liter of dry resin; and
    MSE is said mercaptan sulfur equivalent.

5. A process according to claim 1, wherein said cation exchange resin is a macroporous polystyrene resin cross linked with divinylbenzene.

6. A process according to claim 5, wherein said divinylbenzene is present in an amount ranging between about 5 to about 65% by weight of said cation exchange resin.

7. A process according to claim 5, wherein said divinylbenzene is present in an amount ranging between about 5 to about 35% by weight of said cation exchange resin.

8. A process according to claim 1, further including mixing said alcohol in amounts sufficient to provide a molar ratio of said alcohol to tertiary olefin in said reaction feedstock of between about 0.5 to about 3.

9. A process according to claim 8, wherein said alcohol is selected from the group consisting of methanol, ethanol, propanol, isopropanol, butanol and isobutanol.

10. A process according to claim 1, further including mixing said hydrogen in amounts effective for hydrogenation of diolefin present in said feedstock.

11. A process according to claim 10, further including mixing said hydrogen in amounts sufficient to provide a molar ratio of said hydrogen to diolefin in said reaction feedstock of between about 0.5 to about 4.

12. A process according to claim 1, further including selecting said liquid olefinic hydrocarbon feedstock from the group consisting of a C4–C10 FCC stream, a C4–C10 coking process stream and a C4–C10 steam cracking process stream.

13. A process according to claim 1, wherein said liquid olefinic hydrocarbon feedstock is a light naphtha FCC hydrocarbon stream.

14. A process according to claim 13, wherein said light naphtha stream contains substantially $C_3$–$C_7$ hydrocarbons.

15. A process according to claim 13, wherein said light naphtha stream contains substantially $C_4$ and $C_5$ hydrocarbons.

16. A process according to claim 1, wherein said liquid olefinic hydrocarbon feedstock has a composition as follows:

| | |
|---|---|
| isobutene | 0.1–25 wt % |
| isoamylene | 0.1–30 wt % |
| diolefin | 0.2–2.5 wt % |
| Other $C_4$ and $C_5$ hydrocarbon | 50–90 wt % |
| sulfur | up to about 300 ppm. |

17. A process according to claim 16, wherein said liquid olefinic hydrocarbon feedstock contains sulfur as mercaptan in an amount up to about 80 ppm, as $H_2S$ in an amount up to about 5 ppm, as COS in an amount up to about 5 ppm, as disulfide in an amount up to about 50 ppm, and the balance as other sulfur compounds.

18. A process according to claim 1, wherein said etherification conditions comprise a pressure of between about 10 to about 25 bars gauge, a temperature of between about 40° to about 90° C., and a liquid hourly space velocity of said reaction feedstock to said resin of between about 0.5 to about 5 V/V/hour.

19. A process according to claim 1, wherein said treating step produces an alkyl tert alkyl ether selected from the group consisting of methyl t-butyl ether (MTBE), methyl t-amyl ether (TAME), ethyl t-butyl ether (ETBE) and mixtures thereof.

* * * * *